United States Patent
Ou

Patent Number: 5,756,873
Date of Patent: May 26, 1998

[54] DESIGN FOR AROMATICS ALKYLATION

[75] Inventor: John Di-Yi Ou, Houston, Tex.

[73] Assignee: Exxon Chemical Patents Inc., Houston, Tex.

[21] Appl. No.: 926,093

[22] Filed: Aug. 5, 1992

[51] Int. Cl.$^6$ .................................................. C07C 2/68
[52] U.S. Cl. ........................ 585/467; 585/323; 585/446
[58] Field of Search ........................... 585/323, 446, 585/467

[56] References Cited

U.S. PATENT DOCUMENTS

| | | | |
|---|---|---|---|
| 3,211,799 | 10/1965 | Korelitz et al. | |
| 3,926,842 | 12/1975 | Suggitt et al. | |
| 4,169,111 | 9/1979 | Wight | |
| 4,185,040 | 1/1980 | Ward et al. | |
| 4,400,570 | 8/1983 | Butler et al. | 585/467 |
| 4,683,052 | 7/1987 | Degnan, Jr. et al. | |
| 4,761,513 | 8/1988 | Steacy | 585/467 |
| 4,849,569 | 7/1989 | Smith, Jr. | 585/446 |
| 5,019,669 | 5/1991 | Adams et al. | 585/446 |
| 5,043,506 | 8/1991 | Crossland | 585/449 |

FOREIGN PATENT DOCUMENTS

| | | |
|---|---|---|
| 0 012 514 A1 | 6/1980 | European Pat. Off. |
| 0 433 932 A1 | 9/1991 | European Pat. Off. |
| PCT/US93/07379 | 8/1993 | WIPO |

*Primary Examiner*—Ponnathapura Achutamurthy
*Attorney, Agent, or Firm*—Edward F. Sherer

[57] ABSTRACT

A method is provided for simply and effectively increasing monoalkylation of aromatic compounds while also increasing the life of the acid catalyst used to alkylate said compounds. The method and apparatus involve drastically reducing the amount of the alkylation agent present in the reaction mixture, e.g., to at least about a 99:1 excess of aromatic, preferably to about a 999:1 excess of aromatic. In a preferred embodiment, the alkylation agent is introduced intermittently, or in stages, at a ratio of at least 999:1 so that the excess of aromatic may be maintained at all points in the reactor in order to most effectively prolong the life of the catalyst. For continuous operation, a single reactor equipped with multiple injection ports may be used, or multiple reactors may be connected in series adapted so that the alkylation agent may be introduced prior to each reactor.

24 Claims, 3 Drawing Sheets

SINGLE REACTOR WITH MULTIPLE INJECTIONS

STAGING REACTORS WITH MULTIPLE INJECTIONS

EXPERIMENTAL SETUP
FOR EXAMPLE 2

DESIGN FOR AROMATICS ALKYLATION

FIELD OF THE INVENTION

The present invention relates to a method of alkylating aromatic compounds which maximizes the life of the alkylation catalyst.

BACKGROUND

Solid acid catalysts typically are used to catalyze the alkylation of aromatic compounds. Usually, the aromatic and the alkylating agent are added in a single stage with a slight excess of aromatic to alkylating agent, typically in a range between about 2:1 to 20:1, to reduce the formation of the undesirable heavy products. However, lower excesses of aromatic have been favored because too much excess aromatic was believed to result in less monoalkylation product. See, e.g., U. S. Pat. No. 4,400,570 to Butler, et al., col. 4, 1. 4-6.

One major problem that has been encountered when alkylating aromatics using solid acid catalysts has been rapid deactivation of the catalyst. The root cause of such deactivation appears to lie in the alkylation mechanism, itself. The first step of an alkylation reaction is the formation of a carbonium ion from the alkylation agent and the acid catalyst. If isobutylene is used as the alkylation agent, for instance, the acid catalyst is believed to adsorb isobutylene onto its acidic sites and to turn the isobutylene into tertiary butyl carbonium ions.

Once formed, these carbonium ions have two reaction routes. First, the carbonium ions can add to the aromatic ring and finish the alkylation process. Second, the carbonium ions can react with the remaining alkylation agent to produce high-molecular-weight compounds. For isobutylene, this second reaction route generates products ranging from di-isobutylene up to polyisobutylene. The heavy by-products of the second reaction route can, in turn, alkylate aromatics resulting in even heavier compounds. Products from the second reaction pathway are undesirable because they may deactivate the catalyst by permanently blocking the acidic sites which catalyze the alkylation reaction.

A number of methods have been tried to overcome the problem of deactivation of acid catalysts during the alkylation of aromatics. For example, others have tried: increasing or decreasing the particle size of the catalyst; multiple reaction beds for serial use after deactivation of the catalyst; recycling of the mono- or di-alkylation product back to the initial reaction mixture; and, co-feeding steam along with the aromatic and the alkylating agent. However, a simple and effective method for preventing deactivation of such acid catalysts has not yet been developed.

SUMMARY OF THE INVENTION

The present invention provides a method for simply and effectively increasing the monoalkylation of an aromatic compound while at the same time increasing the life of the acid catalyst used to alkylate the compound. The method involves (a) drastically reducing the amount of the alkylating agent that is present in the reaction mixture, e.g., to at least about an excess of about 99:1 of aromatic, preferably an excess of about 999:1 of aromatic, and (b) introducing the alkylating agent intermittently, or in stages, so that the excess of aromatic may be maintained at all points in the reactor in order to most effectively prolong the life of the catalyst. For continuous operation, a single reactor equipped with multiple injection ports may be used. Alternately, multiple reactors may be connected in series adapted so that the alkylation agent may be introduced prior to each reactor.

DETAILED DESCRIPTION OF THE INVENTION

The present invention may be used to prevent deactivation of a number of acid catalysts during alkylation of aromatic compounds. Such catalysts include zeolites, ion exchange resins, clay, silica, alumina, alumino silicates, and solid acids. The present invention also may be used to prevent the deactivation of such acid catalysts when they are used to alkylate any number of substituted or unsubstituted aromatic compounds. In a preferred embodiment, the invention is used to prevent deactivation of zeolites used to catalyze the alkylation of xylenes and/or alkylbenzenes.

According to the present invention, the reaction mixture to which the catalyst is exposed is comprised of an alkylating agent and an excess of aromatic above about 99:1, preferably above about 500:1, most preferably about 999:1 or above. Lower concentrations of the alkylation agent are preferred because, the higher the concentration of the alkylation agent, the quicker the catalyst will be deactivated.

For example, where an excess aromatic ratio of 99:1 is used during the alkylation of xylene using a zeolite catalyst, the catalyst may be deactivated after only a single day of operation. However, after a full day of alkylation, certain plants may be able to regenerate or replace the catalyst at night without substantial expense or inconvenience. Therefore, regeneration or replacement of a catalyst might be acceptable in some plants. In contrast, however, if an excess of aromatic of approximately 999:1 is used during the alkylation of xylene using a zeolite catalyst, it is possible for the catalyst to remain active for as long as two weeks. Other catalysts may be expected to behave similarly. Therefore, the ideal amount of excess aromatic should be selected according to the particular needs of the plant involved.

Figure 1:
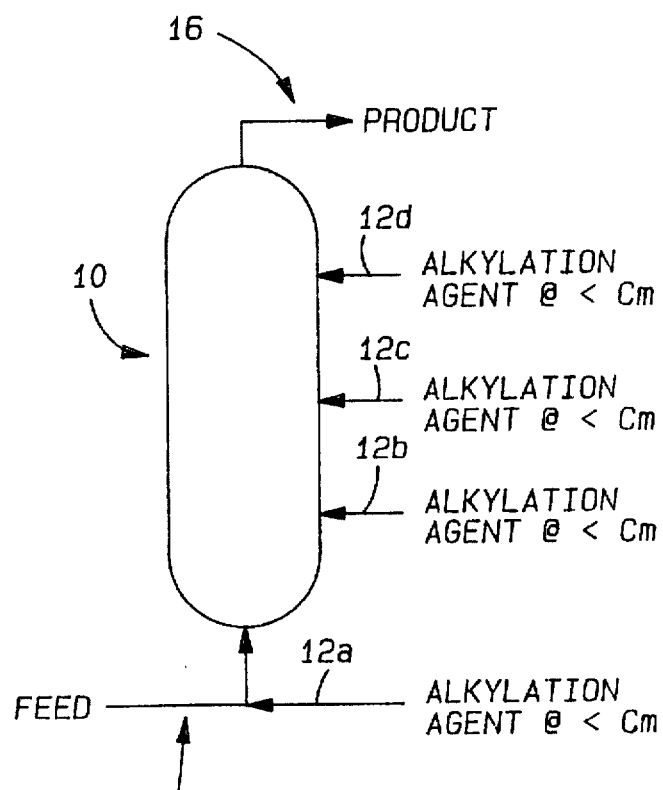
FIG. 1 is a diagrammatic representation of a single reactor having multiple injection ports for use in injecting the alkylation agent according to the present invention.
Figure 2:
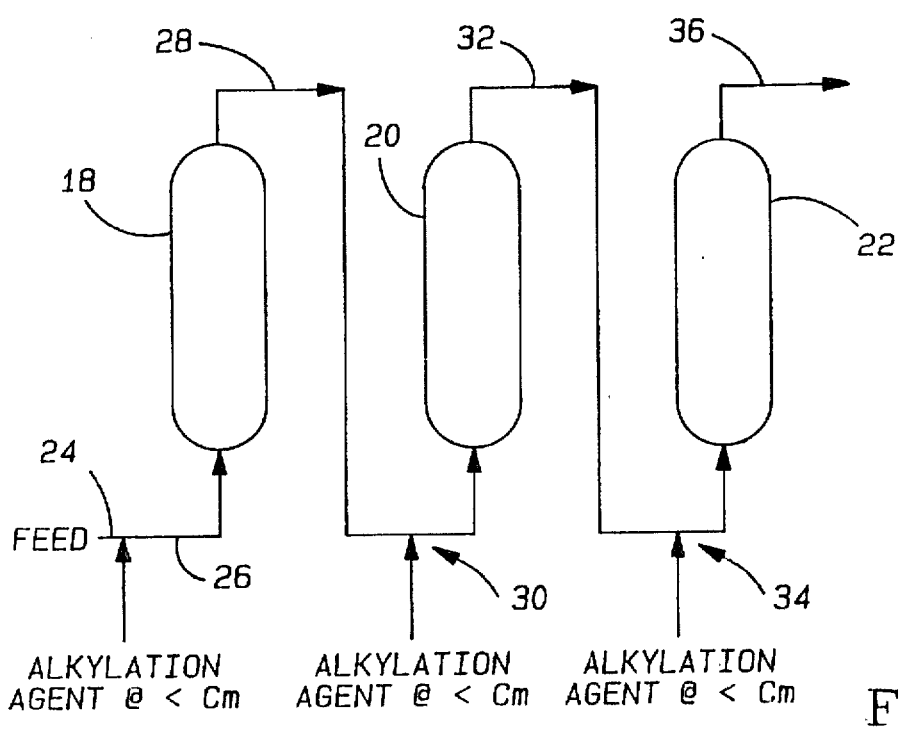
FIG. 2 is a diagrammatic representation of multiple reactors connected in series having injection ports for the alkylation agent just prior to each reactor.

Schematics illustrating the operation of the present invention are shown in FIGS. 1 and 2. For purposes of FIGS. 1 and 2, assume that the concentration of the alkylation agent that should be present in the reaction mixture is "$C_m$" (or less). Referring now to FIG. 1, for continuous operation, a single reactor 10, which is filled with a bed of acid catalyst, has been provided with multiple stages or injection ports 12a–d. One of skill in the art will recognize that reactor 10 and injection ports 12a–d could take many acceptable forms and orientations; therefore, the particular structure of the apparatus diagramed will not be discussed in detail. In FIG. 1, the product feed enters reactor 10 through line 14. An injection port 12a is provided in line 14 before the product feed enters the reactor in order to inject the alkylation agent into the reaction mixture in an amount that will result in a concentration of $C_m$ (or less) of the alkylation agent in the reaction mixture. Of course, reactor 10 should have means for supplying suitable temperatures and pressures for the alkylation of aromatics, e.g., temperatures of less than 500° C. (932° F.), and pressures of less than 1000 psig (6,894,760 Newtons/m$^3$).

As the reaction mixture is pumped through reactor 10, and as the alkylation agent reacts with the aromatic feed, the reaction mixture passes a second injection port 12b which will again inject the alkylation agent in an amount that will result in a concentration of $C_m$ or less of the alkylation agent in the reaction mixture. Additional injections of the alkylation agent occur as the reaction mixture is pumped past injection ports 12c and 12d. At each injection port 12a–d, the amount of alkylation agent that is injected should be carefully set or monitored so that the concentration of alkylation agent in the reaction mixture does not exceed approximately $C_m$. Of course, reactor 10 may be supplied with any number of injection ports 12a–d. Once the reaction mixture is pumped through the reactor 10, the product passes out of reactor 10 through line 16.

FIG. 2 is a diagrammatic representation of an alternate means for intermittently injecting an alkylation agent according to the present invention. As seen in FIG. 2, reactors 18, 20, and 22 are provided in series. The product feed enters the first reactor 18 through line 24. Line 24 is provided with an injection port 26 for injecting the alkylation agent into the product feed before the product feed enters the reactor 18.

The effluent leaves the first reactor 18 via the line 28, which also serves to feed the effluent from reactor 18 into the second reactor 20. Once again, line 28 is provided with an injection port 30 which is positioned, similar to injection port 26, prior to entry into reactor 20. The cycle is then repeated: the effluent exits reactor 20 via line 32; the alkylation agent is added to a concentration of $C_m$ or less via injection port 34 prior to entry of the product stream into reactor 22; and, the effluent exits reactor 22 via line 36. Of course, one could add as many or as few serial reactors a required for specific needs.

The following experiments further illustrate the present invention:

Experiment 1

Figure 3:
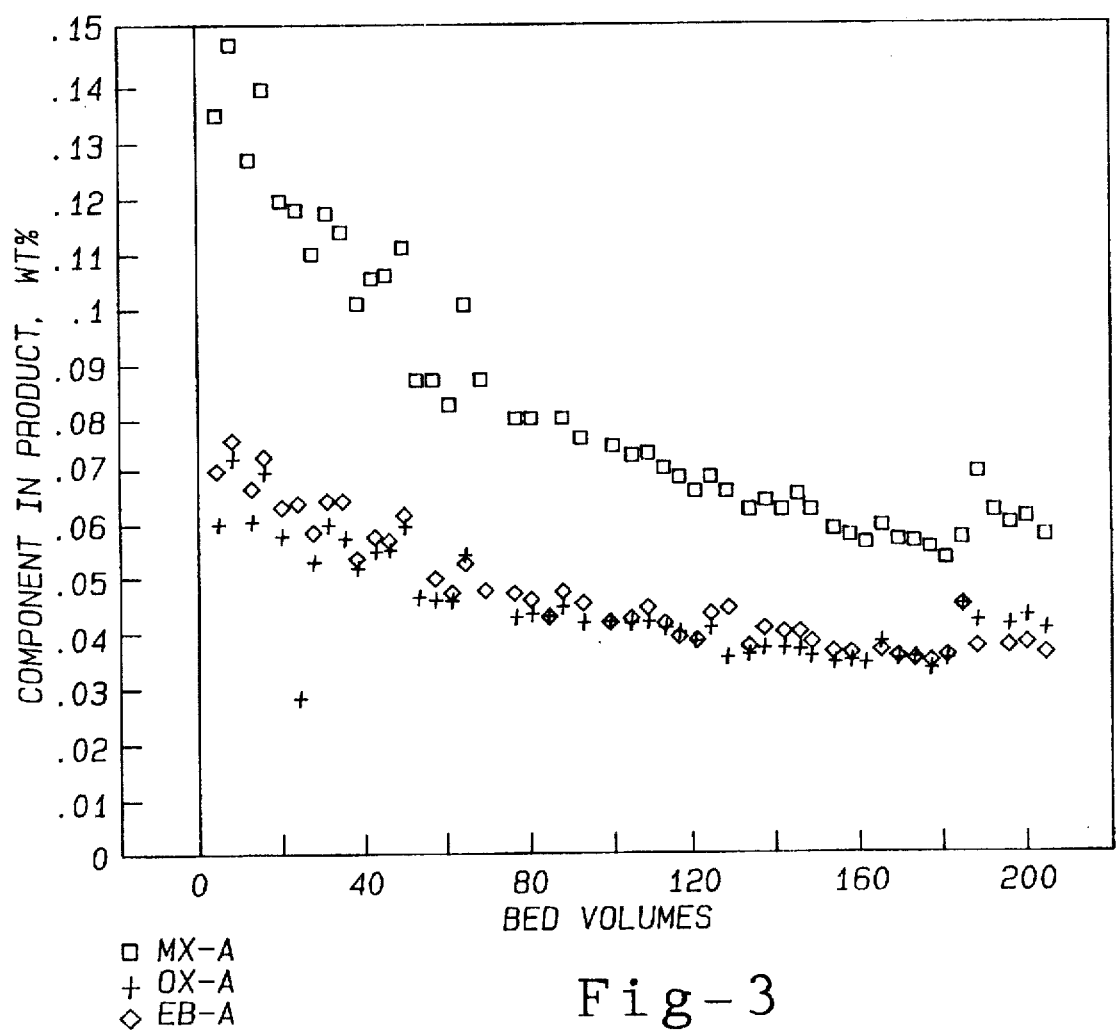
FIG. 3 is a chart illustrating the rate of deactivation of an acid catalyst using conventional alkylation conditions, as described in Experiment 1. The concentration of alkylated meta-xylene, ethylbenzene, and ortho-xylene present in the reaction product are charted as a function of bed volume of feed pumped through the reactor. The yield for all three compounds is shown to decrease steadily with time, indicating gradual catalyst deactivation.

Experiment 1 illustrates the catalyst deactivation problem that usually is seen in a conventional, single stage, fixed-bed alkylation process. The objective of this alkylation process was to selectively alkylate meta-xylene (MX), or ortho-xylene (OX) and ethylbenzene (EB) in the medium of para-xylene (PX) using isobutylene as the alkylation agent. Due to steric hindrance, isobutylene has a higher alkylation selectivity toward MX, OX, and EB than to PX. The feed stream contained 99.746% PX, 0.137% MX, 0.067% EB, and 0.050% OX. The catalyst, a hydrogen-form Y zeolite (LZY-84) provided by UOP Inc., was loaded into a ½"×3½" stainless steel reactor. A mixture of 99.70% feed and 0.30% isobutylene was pumped through the reactor at 1 liquid hourly space velocity (LHSV), 50 psig (344,738 Newtons/m$^3$), and 22° C. (71.6° F). Reaction product was collected periodically and analyzed for xylene and alkylated xylene distributions. FIG. 3 shows the concentration of alkylated MX, EB and OX in product as a function of bed volumes (BV) of feed pumped through the reactor. FIG. 3 illustrates that the yield for all three compounds decreased steadily with time indicating a gradual catalyst deactivation.

Experiment 2

Figure 4:
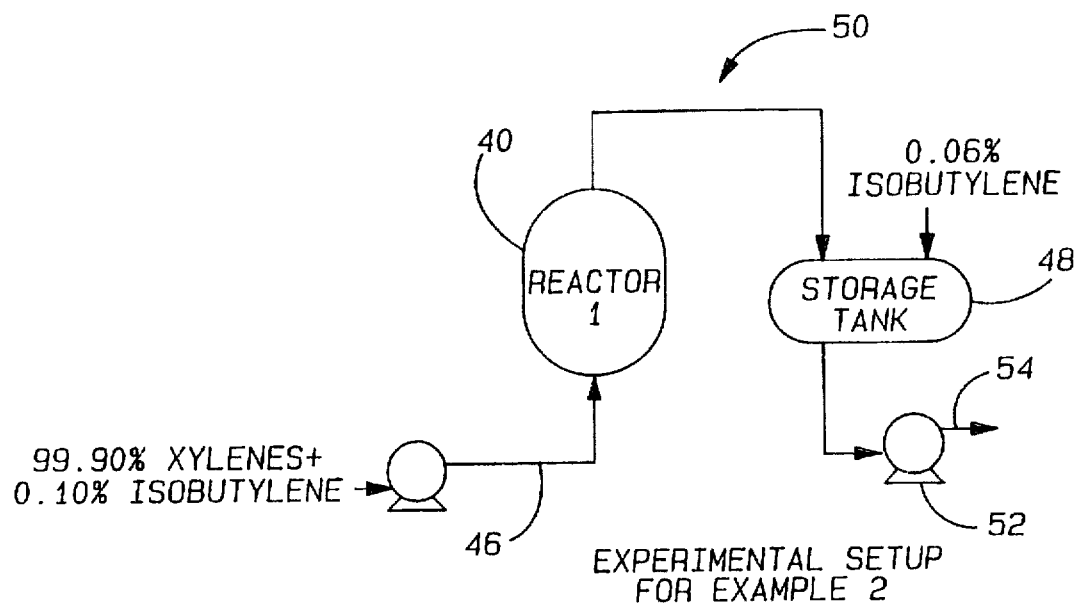
FIG. 4 is a diagrammatic representation of the experimental setup described in Experiment 2.
Figure 5:
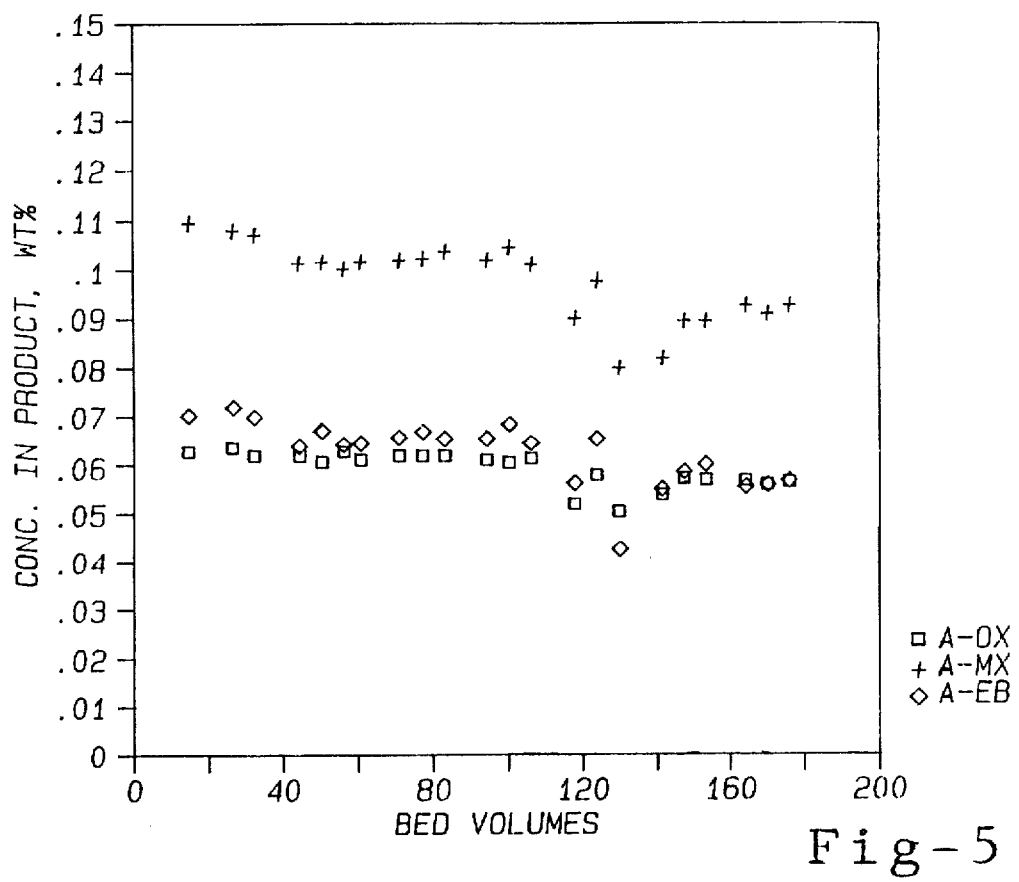
FIG. 5 is a chart illustrating the relatively stable activity of an acid catalyst used in the present process, as described in Experiment 2. Once again, the concentration of alkylated meta-xilene, ethylbenzene, and ortho-xylene present in the product are charted as a function of bed volume of feed pumped through the reactor. The yield for all three compounds decreased much more slowly with time than the decrease seen in FIG. 3, indicating much slower catalyst deactivation using the present invention.

This experiment illustrates the advantage of the present invention with respect to catalyst stability and yields. FIG. 4 is a diagrammatic representation of the set up used in this experiment. Referring to FIG. 4, two ½"×1¾" reactors 40, 42 were arranged serially. The volume of each of the two reactors was exactly half of the reactor volume in Experiment 1. The same xylene stream used in Experiment 1 was used for feed. A mixture of 99.90% feed and 0.10% isobutylene was pumped via line 46 into the first reactor 40 at 2 LHSV, 50 psig (344,738 Newtons/m$^3$), and 22° C. C. (71.6F). The effluent from the first reactor 40 then was pumped to storage tank 48 via line 50. In storage tank 48, 0.06% isobutylene was added to the product stream. The product stream then was pumped from storage tank 48 by pump 52 through line 54 and into the second reactor 42, and maintained at the same conditions as in the first reactor 40. It should be pointed out that, although the individual flow rate for each reactor was 2 LHSV, the overall flow rate for the two reactors in series was 1 LHSV. The concentration of alkylated MX, OX, and EB is plotted in FIG. 5. From FIG. 5, it is seen that the present invention provides a more efficient use of isobutylene (0.16% vs. 0.30%) with similar initial yields to those from Experiment 1. The present invention also provides much greater catalyst stability, as demonstrated by the relatively stable yields for all three compounds.

Experiment 3

Figure 6:
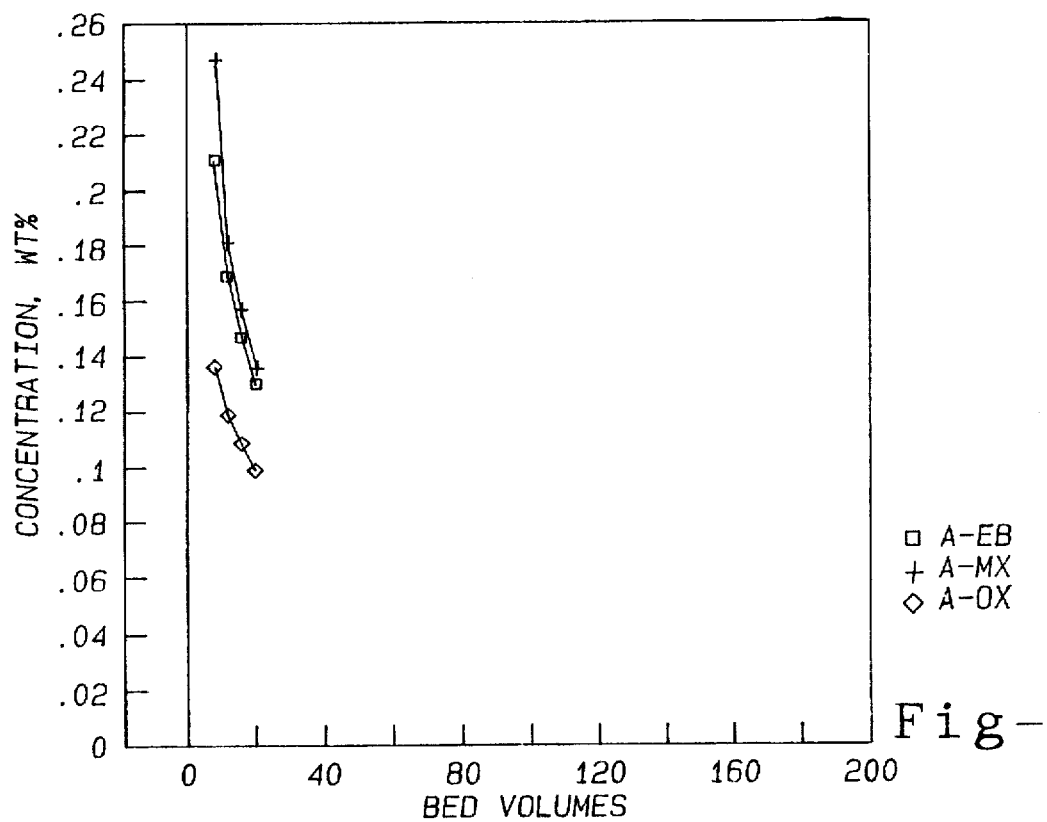
FIG. 6 is a chart illustrating the concentration of alkylated ethylbenzene, meta-xylene, and ortho-xylene present in the product charted as a function of bed volumes of feed pumped through the reactor. The catalyst was deactivated faster than under the conditions of FIG. 5.

This experiment illustrates the alkylation results at a hydrocarbon to isobutylene ratio of 99:1, with no staging of the reaction. The hydrocarbon stream used in this experiment contained 98.98% para-xylene, 0.49% meta-xylene, 0.33% ethylbenzene, and 0.20% ortho-xylene. A mixture of 99.00% hydrocarbon and 1.00% isobutylene was pumped through a ½"×1¾" stainless steel reactor packed with LZY-84 catalyst at 1 LHSV, 50 psi (344,738 Newtons/m$^3$), and 22° C. Reaction product was collected periodically and analyzed for xylene and alkylated xylene distribution. FIG. 6 shows the concentration of alkylated ethylbenzene, meta-xylene, and ortho-xylene in the reaction product as a function of the bed volumes of feed pumped through the reactor. The catalyst was deactivated faster than under the conditions of Experiment 2.

One of skill in the art will appreciate that many modifications may be made to the embodiments described herein and explained in the accompanying figures without departing from the spirit of the present invention. Accordingly, the embodiments described herein are illustrative only and are not intended to limit the scope of the present invention.

I claim:

1. A process for alkylating aromatic compounds comprising passing a mixture of an amount of alkylation agent and a molar excess of aromatic hydrocarbon of at least about 99:1 over an acid catalyst in a reactor under alkylating conditions sufficient to result in an alkylation of said aromatic hydrocarbon thereby depleting said alkylation agent with minimized deactivation of said alkylation catalyst;

introducing additional amounts of alkylation agent to said alkylatable aromatic hydrocarbon in stages to replenish depleted alkylation agent in said mixture to continue said alkylation while preventing rapid deactivation of said catalyst; and recovering a desired alkylated aromatic hydrocarbon.

2. The process of claim 1 wherein said molar excess of aromatic hydrocarbon is at least about 500:1.

3. The process of claim 1 wherein said molar excess of aromatic hydrocarbon is at least about 900:1.

4. The process of claim 1 wherein said molar excess of aromatic hydrocarbon is at least about 999:1.

5. The process of claim 1 wherein said aromatic hydrocarbon comprises a xylene and said acid catalyst is a zeolite.

6. The process of claim 2 wherein said aromatic hydrocarbon comprises a xylene and said acid catalyst is a zeolite.

7. The process of claim 2 wherein said aromatic hydrocarbon comprises a xylene and said acid catalyst is a zeolite.

8. The process of claim 3 wherein said aromatic hydrocarbon comprises a xylene and said acid catalyst is a zeolite.

9. The process of claim 5 wherein said alkylation is conducted at a temperature in the range of about 10° C. to about 300° C.

10. The process of claim 8 wherein said alkylation is conducted at a temperature in the range of about 10° C. to about 300° C.

11. The process of claim 5 wherein said alkylation is conducted at a LHSV between about 0.1 and about 100.

12. The process of claim 8 wherein said alkylation is conducted at a LHSV between about 0.1 and about 100.

13. The process of claim 5 wherein said alkylation is conducted at a pressure from sub-atmospheric to about 1000 psig.

14. The process of claim 8 wherein said alkylation is conducted at a pressure from sub-atmospheric to about 1000 psig.

15. A process for alkylating aromatic compounds comprising:

passing a mixture of an amount of alkylation agent and a molar excess of at least about 99:1 of an alkylatable aromatic hydrocarbon over a fixed bed acid catalyst in a reactor under alkylating conditions sufficient to result in alkylation of said aromatic hydrocarbon thereby depleting said alkylation agent with minimized deactivation of said alkylation catalyst;

introducing additional amounts of alkylation agent to said alkylatable aromatic hydrocarbon in stages, to replenish depleted alkylation agent in said mixture to continue said alkylation while preventing rapid deactivation of said catalyst; and recovering a desired alkylated aromatic hydrocarbon.

16. The process of claim 15 wherein said molar excess of aromatic hydrocarbon is at least about 999:1.

17. The process of claim 15 wherein said aromatic hydrocarbon comprises a xylene and said acid catalyst is a zeolite.

18. The process of claim 16 wherein said aromatic hydrocarbon comprises a xylene and said acid catalyst is a zeolite.

19. The process of claim 15 wherein said alkylation is conducted at a temperature in the range of about 10° C. to about 300° C.

20. The process of claim 18 wherein said alkylation is conducted at a temperature in the range of about 10° C. to about 300° C.

21. The process of claim 15 wherein said alkylation is conducted at a LHSV between about 0.1 and about 100.

22. The process of claim 18 wherein said alkylation is conducted at a LHSV between about 0.1 and about 100.

23. The process of claim 15 wherein said alkylation is conducted at a pressure from sub-atmospheric to about 1000 psig.

24. The process of claim 18 wherein said alkylation is conducted at a pressure from sub-atmospheric to about 1000 psig.

* * * * *